(12) United States Patent  (10) Patent No.: US 7,726,564 B2
Goldbach  (45) Date of Patent: Jun. 1, 2010

(54) MEDICAL INSTRUMENT IDENTIFICATION

(75) Inventor: Günter Goldbach, Wörth/Wifling (DE)

(73) Assignee: BrainLAB AG, Feldkirchen (DE)

( * ) Notice: Subject to any disclaimer, the term of this patent is extended or adjusted under 35 U.S.C. 154(b) by 2 days.

(21) Appl. No.: 12/024,128

(22) Filed: Feb. 1, 2008

(65) Prior Publication Data
US 2008/0185430 A1 Aug. 7, 2008

Related U.S. Application Data

(60) Provisional application No. 60/895,498, filed on Mar. 19, 2007.

(30) Foreign Application Priority Data
Feb. 1, 2007 (EP) .................................. 07002217

(51) Int. Cl.
*G06F 19/00* (2006.01)
(52) U.S. Cl. ...................................................... 235/385
(58) Field of Classification Search ................. 235/385; 705/28; 600/427
See application file for complete search history.

(56) References Cited

U.S. PATENT DOCUMENTS

| | | | |
|---|---|---|---|
| 6,675,040 B1 * | 1/2004 | Cosman | 600/427 |
| 6,690,964 B2 * | 2/2004 | Bieger et al. | 600/424 |
| 6,738,656 B1 * | 5/2004 | Ferre et al. | 600/426 |
| 6,934,575 B2 * | 8/2005 | Ferre et al. | 600/427 |
| 7,043,961 B2 * | 5/2006 | Pandey et al. | 73/1.81 |
| 7,477,926 B2 * | 1/2009 | McCombs | 600/407 |
| 2002/0198451 A1 * | 12/2002 | Carson | 600/424 |
| 2005/0203544 A1 * | 9/2005 | Revie et al. | 606/130 |
| 2005/0251186 A1 | 11/2005 | Revie et al. | |
| 2006/0200025 A1 * | 9/2006 | Elliott et al. | 600/424 |

FOREIGN PATENT DOCUMENTS

| | | |
|---|---|---|
| DE | 42 05 406 | 9/1993 |
| WO | 99/38449 | 8/1999 |
| WO | 04/001569 | 12/2003 |
| WO | 2004/030560 | 4/2004 |
| WO | 2006/060631 | 6/2006 |

* cited by examiner

*Primary Examiner*—Thien M. Le
*Assistant Examiner*—April A Taylor
(74) *Attorney, Agent, or Firm*—Renner, Otto, Boisselle & Sklar, LLP

(57) ABSTRACT

A medical instrument identification system for identifying a medical instrument from a plurality of medical instruments includes at least one optical sensor for detecting features of the at least one medical instrument, and a data processing device operatively coupled to the at least one optical sensor. The data processing device is operative to use videometric pattern recognition to identify the at least one medical instrument based on the detected features, wherein the optical sensor and the data processing device are assigned to a medical instrument tracking system.

22 Claims, 2 Drawing Sheets

MEDICAL INSTRUMENT IDENTIFICATION

RELATED APPLICATION DATA

This application claims priority of U.S. Provisional Application No. 60/895,498 filed on Mar. 19, 2007, which is incorporated herein by reference in its entirety.

FIELD OF THE INVENTION

The invention relates to medical navigation and, more particularly, to medical instrument identification.

BACKGROUND OF THE INVENTION

In the field of medical navigation, in which, for example, surgical instruments are located, positionally tracked and displayed on an image display system (monitor) together with patient structures (e.g., for image-assisting the treatment), it is often necessary and advantageous to unambiguously identify the instruments. This is particularly true when working with so-called pre-calibrated instruments, i.e., instruments whose external shape and function have already been stored in advance in a data memory of the medical navigation system. During medical navigation, these instruments can be automatically identified. Based on this identification, the navigation system has enough information concerning the instrument to correctly navigate the instrument.

WO 2004/001569 A2, for example, has already proposed using a separate barcode reader to identify such instruments. This has the disadvantageous effect that the instruments have to be guided to the barcode reader prior to use, which exhibits a relatively small visual range. Naturally, additional costs also arise for acquiring, handling and maintaining the barcode reader.

SUMMARY OF THE INVENTION

A system in accordance with the invention recognizes a medical instrument that can be used within the framework of medical navigation. The system includes one or more optical sensor(s) and a data processing device for identifying features of the instrument that are detected by the sensor. The optical sensor and the data processing device are assigned to and/or integrated into a medical instrument tracking system, and the data processing device comprises videometric pattern recognition.

In navigation-assisted treatments, a tracking system such as has been described above is typically used to locate and track the instruments. The system and method in accordance with the invention integrates another function into the tracking system, by also assigning the optical sensor and the data processing device for instrument identification to said instrument tracking system. Advantageously, this optimally uses hardware already present, and because the visual range of such tracking systems is usually relatively large, the instruments do not have to be separately passed in front of a reader in order to integrate them into the navigation environment.

The data processing device can be connected to or integrated into the data processing of the tracking system. The data processing, however, also can be connected to or integrated into the data processing of a medical navigation system assigned to the tracking system.

The optical sensor can be formed by the tracking sensor or tracking sensors of the tracking system. A tracking system in the field of medical navigation technology often comprises a stereoscopic camera system that can positionally detect instruments or apparatus within the treatment environment, and in accordance with the present invention can in principle also take on the identification function. It is also possible to use as the optical sensor a sensor, such as a CMOS or CCD sensor, that is provided in addition to the tracking sensors of the tracking system and, for example, arranged on the tracking system.

One or more identification patterns can be attached to the instrument, such as a barcode, a text pattern or a color code, wherein other optically detectable codes can also be used. The identification pattern can be attached to a replaceable part of the instrument, such as an exchangeable functional part, e.g., a plug-type drill sleeve that can be placed on a navigated handle (comprising a reference array). The identification pattern can be attached in such a way that it is visible from different angles of view and correspondingly extends over the surface of the instrument.

The instrument, an individual part of the instrument, or the entire instrument (including its combined individual parts) can exhibit an external shape that can be unambiguously identified from a group of such instruments. An instrument thus can be identified in accordance with the invention by one or more attached patterns, by its external shape (contour) or by both features.

In a method in accordance with the invention for identifying a medical instrument that can be used within the framework of medical navigation, identification features of the instrument are detected using one or more optical sensor(s) assigned to a medical instrument tracking system, and data from the sensors are provided to a data processing device. The data processing device can be assigned to the medical instrument tracking system. The data concerning the identification features can be processed, for example, by means of videometric pattern recognition, and the instrument can be identified on the basis of the processed data. One advantage of the method is that it can be performed using the device elements and device functions already in place in the medical theater.

A multiple-part instrument including a group of instrument parts that comprise a common or same base part can be identified by the particular part attached to the base part (e.g., the particular part bears the code or exhibits a unique external shape).

A tracking sensor or tracking sensors of the tracking system and a sensor that is provided in addition to the tracking sensors of the tracking system (e.g., arranged on the tracking system) can be used as the optical sensor, wherein the data processing device for identifying the instrument can either evaluate the data of the sensor or sensors providing the most reliable data (based the current location of the instrument) or can combine the data of a number of sensors and evaluate them together.

Also provided is a program which, when it is running on a computer or is loaded on a computer, causes the computer to perform a method as described above, and a computer program storage medium comprising such a program.

One feature of the system and method in accordance with the present invention is that available technology for medical applications is used, and different technologies can be combined with and/or integrated into specific medical applications. In the present case, marker-based surgical image-assistance systems and/or medical navigation systems, and specifically their optical tracking systems using videometric pattern recognition technology, can be combined for use in a new and improved medical application, so as to increase the safety and efficiency of the systems.

One problem in conventional optical tracking systems is that the number of different rigid marker geometries which can be used for instrument identification is limited. Problems with the marker recognition, accuracy and reliability of the tracking system can also occur, as well as practical limitations in its handling which relate to the size and weight of the instruments and/or marker reference arrays.

The system and method in accordance with the invention expand the functionality of the navigation tracking systems to include particular types of pattern recognition, specifically also in combination with marker detection. This involves suitably illuminating and recognizing characteristic patterns on the instrument, and a means which can automatically assign the information to a combination of tools. On the basis of the spatial arrangement of the rigid marker reference arrays, it is also possible to predict the area in which the identification pattern may be expected so as to improve the reliability of the system.

The system and method can differentiate between a number of instruments that use the same rigid reference marker geometry or arrangement, for example by using a common handle that can bear a number of functional parts of the instrument. By recognizing the identification features on the instrument (e.g., on the functional part), the tracking system can look up specific geometric information for the particular instrument in a database, and the position of the instrument tip and/or of the functional part of the instrument can be calculated without having to separately calibrate the instrument.

One advantages of the system in accordance with the invention thus includes a reduction in the number of recognizable reference arrays (marker array geometries), which is seen in particular when using a number of versions of instruments having the same rigid reference array (marker geometry). A good example is a drill sleeve, such as is specifically used in orthopaedic applications. This instrument consists of a handle that exhibits a reference geometry on its rigid base body, and a sleeve that is available in a number of variations, depending on the drill diameter and the shaft length. For the surgeon, it is then important to ensure that the tracking system or navigation system knows which combination of instruments is actually being used at a particular point in time. Otherwise, it would not be possible to use pre-calibrated instruments, and the tip of each instrument would have to be calibrated relative to the tracked rigid base body (reference array). In accordance with the prior art, the user was then often provided with lists on the navigation monitor, in which he could select the actual instrument. Disadvantageously, however, this requires further interaction with the system and can be a source of errors.

The system and method for instrument identification in accordance with the invention reduces the interaction with the navigation system in this regard and thus simplifies the procedure. It also reduces the risk of manually selecting the wrong instrument, which could cause serious problems. It makes it easier to modify known instruments and surgical tools which are often used; no additional weight is applied, and there is no need for additional parts or markers. The system and method do not have any negative effect on the safety and reliability of the instrument itself and do not involve any substantial increases in costs, since only minor modifications to existing systems are made. Existing instruments or tools can also be adapted in accordance with the invention using an "upgrade", at relatively little cost, because it is often only necessary to attach a pattern to the instrument. It is possible to use techniques for equipping the instrument with identification features that do not have any negative effect on the sterility of the instrument and do not make it more difficult to disinfect or clean it (e.g., laser engraving on high-grade steel instruments).

BRIEF DESCRIPTION OF THE DRAWINGS

The forgoing and other features of the invention are hereinafter discussed with reference to the drawing.

DETAILED DESCRIPTION

Figure 1:
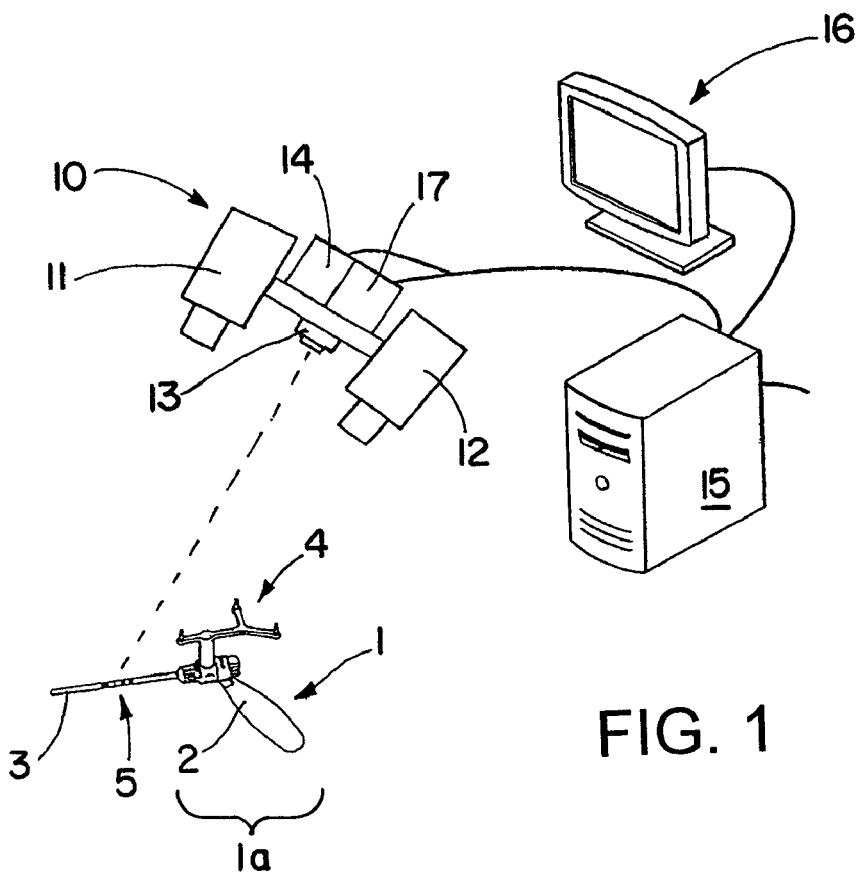
FIG. 1 is a schematic diagram of an exemplary medical instrument identification system in accordance with the invention.

With reference to FIG. 1, an exemplary surgical instrument 1 includes a handle 2 and a navigation reference array 4 to which three reflection marker spheres can be attached. The handle 2 and the reference array 4 are rigidly connected to each other and together form a base part 1a of the instrument 1.

Figure 2:
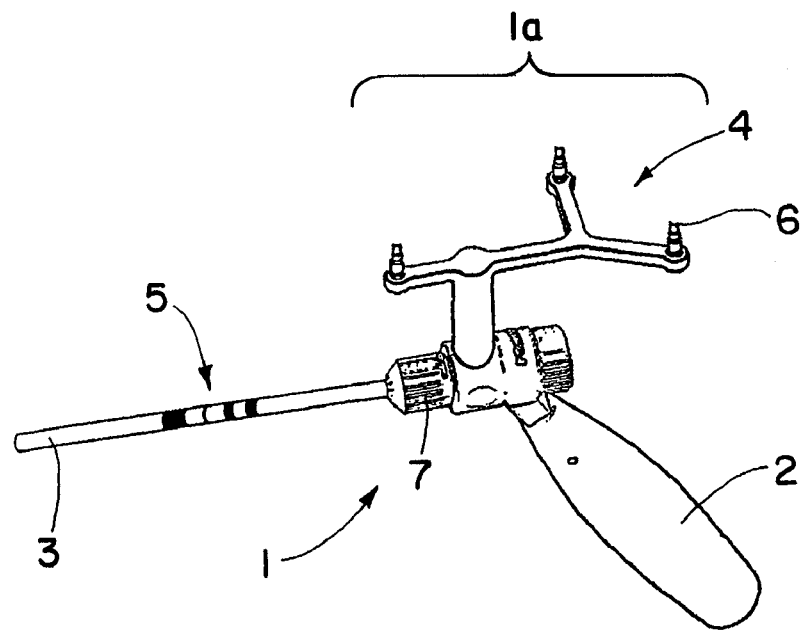
FIGS. 2 and 3 illustrate examples of medical instruments provided with an identification pattern in accordance with the invention.

Additionally, the instrument 1 also comprises a replaceable functional part, such as a drill sleeve 3, for example, in which the instrument is a surgical drill guide. The drill sleeve 3 can be plugged onto or otherwise connected to the base part 1a and comprises the adaptor 7 (see FIGS. 2 and 3) for this purpose. The above reference signs apply not only to FIG. 1 but also to the two different instruments shown in FIGS. 2 and 3.

The instrument 1 can be located and positionally tracked in a navigation environment by a tracking system 10. The tracking system 10 can be a stereoscopic tracking system comprising two cameras 11 and 12 that positionally detect markers (not shown) arranged on the reference array 4 of the instrument 1. By stereoscopic detection, the spatial location of the instrument 1 can be detected three-dimensionally in terms of coordinates. As with normal navigation systems, the tracking system 10 processes the position data in a data processing unit 17 and relays the data to a navigation system, which in this case is schematically shown by a computer 15 and a monitor 16.

Figure 3:
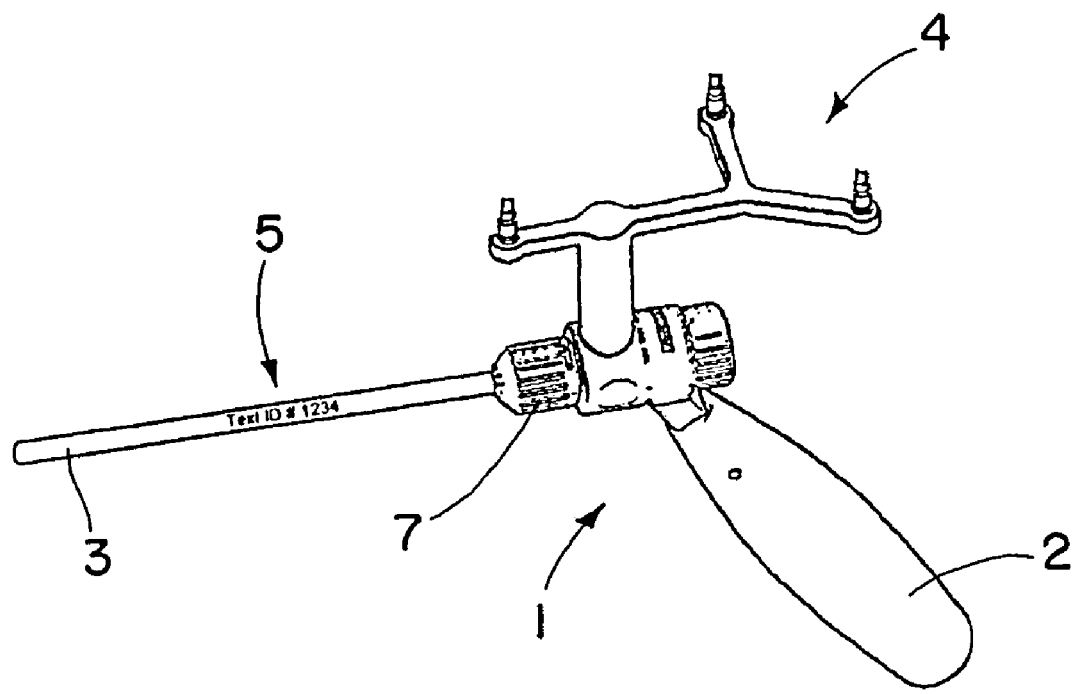

In accordance with one embodiment of the invention, a video camera 13 attached to the tracking system 10 can be used to record an image of an identification pattern 5 attached, for example, to the sleeve 3 of the instrument 1. In the present case, the pattern 5 takes the form of a sort of barcode and encircles the drill sleeve 3 such that is visible from all sides of the instrument. The system and method in accordance with the invention are not limited to this sort of barcode arrangement for identification. Other identification patterns, such as text markings, also can be used, as shown in FIG. 3. The text also can be arranged repeatedly around the instrument shaft (drill sleeve 3). If different drill sleeves are used, they will have different identification features.

By detecting the features with the aid of the camera 13 (e.g., a CMOS or CCD sensor) as described above, the navigation system 15 is informed as to which drill sleeve is currently being used. The navigation system can have stored thereon or have access to a list comprising different drill sleeves and, therefore, knows the length and arrangement of each individual drill sleeve on the instrument 1 and the position of its tip and the spatial arrangement (via the reference array 4). In the example shown in FIG. 1, a data processing means 14 is additionally indicated schematically on the tracking system, and is responsible for processing the identification features and relaying them to the navigation system 15. It is, however, also in principle possible to merely detect the identification features 5 using the tracking system and to perform the subsequent processing completely in the navigation system 15. The data processing means 14 (identification) and 17 (navigation) can of course also be combined to form a single data processing unit comprising both functions.

Pattern recognition can be performed within the range of visible light or, in the case of non-visible wavelengths, in the infrared or UV range. It is in principle possible to omit the separate imaging means 13 and have the tracking cameras 11 and 12 also detect the identification pattern 5. To this end, it would be possible to adapt the illumination or amplification and the shutter settings on the tracking system cameras such that can fulfil both their tracking function and the identification function.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical instrument identification system for identifying a medical instrument from a plurality of medical instruments, comprising:
    a base part including a plurality of trackable markers attached thereto;
    at least one functional part configured for attachment to the base part, the at least one functional part including at least one unique identification feature different from the trackable markers;
    at least one optical sensor configured to detect the at least one identification feature of the at least one functional part when attached to the base part; and
    a data processing device operatively coupled to said at least one optical sensor, said data processing device operative to use videometric pattern recognition to identify the at least one functional part based on the detected identification feature, wherein the optical sensor and the data processing device are assigned to a medical instrument tracking system.

2. The medical instrument identification system according to claim 1, wherein the data processing device is connected to or integrated within a data processor of the tracking system.

3. The medical instrument identification system according to claim 1, wherein the data processing device is connected to or integrated within a data processor of a medical navigation system assigned to the tracking system.

4. The medical instrument identification system according to claim 1, wherein the optical sensor comprises a tracking sensor or tracking sensors of the tracking system.

5. The medical instrument identification system according to claim 1, wherein the optical sensor comprises a CMOS or CCD sensor arranged on the tracking system.

6. The medical instrument identification system according to claim 5, wherein the optical sensor is a sensor used by the tracking system for tracking the medical instrument.

7. The medical instrument identification system according to claim 1, wherein the at least one identification feature comprises a plurality of identification features attached to or formed on each functional part of the at least one functional part.

8. The medical instrument identification system according to claim 7, wherein the plurality of identification features comprise at least two of a barcode, a text pattern or a color code.

9. The medical instrument identification system according to claim 7, wherein the at least one identification feature encircles a surface of the at least one functional part and are visible about a 360 degree view around the at least one functional part.

10. The medical instrument identification system according to claim 1, wherein the data processing device is operable to identify the instrument, an individual part of the instrument, or a combination of individual parts of the instrument from a group of such instruments, said identification based on an external shape of said instrument.

11. The medical instrument identification system according to claim 1, wherein the at least one optical sensor is further configured to detect a spatial position of the trackable markers, and to determine a spatial position of the at least one functional part when attached to the base part based on the detected spatial position and the detected identification feature.

12. A method for identifying a medical instrument from a plurality of medical instruments, the medical instrument including a base part having a plurality of trackable markers attached thereto, and at least one functional part removably attachable to the base part, the at least one functional part including at least one unique identification feature, the method comprising:

using at least one optical sensor assigned to a medical instrument tracking system to detect the at least one unique identification feature of the at least one functional part;

using a data processing device that implements videometric pattern recognition to process the detected at least one identification feature, said data processing device assigned to the tracking system; and identifying the at least one functional part attached to the base part based on the processed at least one identification feature.

13. The method according to claim 12, wherein using at least one optical sensor to detect the at least one identification feature includes using a sensor that is provided in addition to tracking sensors of the tracking system as the optical sensor.

14. The method according to claim 13, wherein using the sensor provided in addition to the tracking sensor or tracking sensors includes arranging a CMOS or CCD sensor on the tracking system.

15. The method according to claim 12, wherein using at least one optical sensor includes using a tracking sensor or tracking sensors of the tracking system as the optical sensor.

16. The method according to claim 12, wherein using at least one optical sensor includes using a tracking sensor or tracking sensors of the tracking system and a sensor that is provided in addition to the tracking sensor or tracking sensors of the tracking system as the optical sensor.

17. The method according to claim 16, wherein using the tracking sensor or tracking sensors of the tracking system and the additional sensor includes:

evaluating sensor data from each sensor to determine which sensor or sensors provide more robust data; or combining data of a number of sensors and using the combined data as sensor data.

18. The method according to claim 17, wherein evaluating sensor data includes determining, based on the sensor data, which sensor has a more robust view of the instrument.

19. The method according to claim 12, wherein detecting the at least one unique identification feature includes using a barcode, a text pattern or a color code as the identification feature.

20. The method according to claim 12, wherein identifying the instrument includes identifying the instrument from a group of instruments based on an external shape of the instrument, an individual part of the instrument or a combination of individual parts of the instrument.

21. The method according to claim 12, wherein identifying the instrument includes identifying based on an external shape of the functional part or on an identification code attached to or formed on the functional part.

22. A non-transitory computer readable storage medium with an executable program stored thereon for identifying a medical instrument from a plurality of medical instruments, the medical instrument including a base part having a plurality of trackable markers attached thereto, and at least one functional part removably attachable to the base part, the at least one functional part including at least one unique identification feature, wherein the program instructs a processor to perform the following steps:

use data from at least one optical sensor assigned to a medical instrument tracking system to detect the at least one unique identification feature of the at least one functional part;

implement via the processor videometric pattern recognition to process the detected at least one identification feature; and identify the at least one functional part attached to the base part based on the processed at least one identification feature.

* * * * *